US00PP08367P

United States Patent [19]

DeCoster

[11] Patent Number: Plant 8,367

[45] Date of Patent: Sep. 7, 1993

[54] SPATHIPHYLLUM PLANT NAMED SPARKLE

[75] Inventor: Paul DeCoster, Melle, Belgium

[73] Assignee: Cari Mar International, Inc., Miami, Fla.

[21] Appl. No.: 840,188

[22] Filed: Feb. 24, 1992

[51] Int. Cl.[5] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

A new and distinct Spathiphyllum plant named Sparkle, characterized by its full and well branched habit, dark green, thick and leathery leaves, numerous relatively small flowers held closely above the foliage on strong pedicels, with the flowering habit resulting in substantially less cubic feet being required for shipping.

2 Drawing Sheets

The present invention comprises a new and distinct cultivar of Spathiphyllum, botanically known as Spathiphyllum and referred to by the cultivar name Sparkle.

The new cultivar is a product of a planned breeding program, and was originated from a cross made by the inventor Paul DeCoster in Melle, Belgium.

The female, or seed pollen parent was Tasson, and the male, or pollen parent was Petite.

Sparkle was discovered and selected as a flowering plant within the progeny of the stated cross by the inventor in a controlled environment in Melle, Belgium, and identified as seedling No. 12. Subsequent asexual reproduction by tissue culture has demonstrated that the combination of characteristics as herein disclosed for the new cultivar are firmly fixed and are retained through successive generations of asexual reproduction.

The following traits has been repeatedly observed and in combination distinguish Sparkle as a new and distinct cultivar:

1. Full, well branched, medium size.
2. Dark green leaves which are thick and leathery.
3. Numerous relatively small flowers held closely above (approximately 10–20 cm) the foliage on strong pedicels. Such flower positioning requires substantially less cubic feet for shipment in boxes.

BRIEF DESCRIPTION OF THE VARIOUS VIEWS OF THE DRAWING

In the color photographic drawings, on the first sheet of the drawing, the photo at the top is a front perspective view of a typical specimen of 'Sparkle'.

The lower photograph comprises an enlarged showing of a typical leaf of 'Sparkle'.

The photo of the second sheet is an enlarged showing of the flower parts of the plant. The number "12" appearing in the drawing refers to the seedling number given to the new variety, as above noted.

BOTANICAL DESCRIPTION

The following observations, measurements and values describe plants grown in Homestead, Fla. under greenhouse conditions which closely approximate those generally used in horticultural practice. Color references are made to The Royal Horticultural Society (R.H.S.) Color Chart, except where general color terms of ordinary significance are used. The color values were determined between 10:00–12:00 a.m. on Jun. 13, 1991 under 100 foot candles of artificial light at Homestead, Fla.

The new cultivar can be compared to the well known cultivar Viscount and the female parent Tasson. Similarities between all three cultivars are medium plant size and glossy leaves. Sparkle is distinguished from both cultivars by its thicker and more leathery dark green leaves carried on stiff petioles, cupped, more upright flowers, better flower production, and its more compact habit.

Classification:

*Botanical.*—Spathiphyllum cv. Sparkle.

*Commercial.*—Spathiphyllum.

Parentage:

*Male parent.*—Petite.

*Female parent.*—Tasson.

Propagation: By tissue culture.

Plant: From 32 cm to 41 cm tall (above soil level) when grown in 25 cm pots, and approximately 91 cm in diameter when fully grown.

*Growth habit.*—Medium size, well branched, full.

Leaves:

*Form and size.*—Simple, elliptic to ovate with acuminate apices and obtuse base. Leaf blade entire. Leaf blade width is slightly asymmetrical with respect to midvein. Apices typically curled.

*Texture.*—Smooth, thick, leathery, glossy or polished.

*Veins.*—Sunken, midvein prominent.

*Color.*—Upper Surface: Green 137A. Lower Surface: Green 137C.

Flowers:

*Buds.*—Spathe tightly rolled around spadix and extrudes from petiole sheath. Spathe is fully opened when pedicel is fully elongated approximately 40 cm to 50 cm above soil level.

Spathe:

*Size.*—8 cm to 9.5 cm wide by 12 cm to 14 cm long.

*Color (RHS).*—White 155C.

*Arrangement.*—Carried on straight, upright, on strong pedicels 10–20 cm above foliage.

*Shape.*—Ovate with curled acuminate apices, obtuse base narrowly decurrent on pedicel.

*Flowering.*—Flowers naturally in 8–10 months from tissue culture. Seasonally free flowering in January through May, and can be forced to flower at other times with Giberillic acid.

Spadix:

*Size.*—3 cm to 7 cm long depending on maturity of plant.

*Color (RHS).*—Yellow-White 158B.

*Longevity.*—Flowers remain white for approximately 30–45 days and slowly regress to a green color.

*Other characteristics.*—Held above foliage 10 cm to 20 cm on strong pedicels.

Reproductive organs:

*Anthers and filaments.*—Not clearly visible.

Roots: Fleshy main roots with fine lateral roots.

Disease resistance: Resistant to Phytophthora.

I claim:

1. A new and distinct cultivar of Spathiphyllum plant named Sparkle, as illustrated and described.

* * * * *

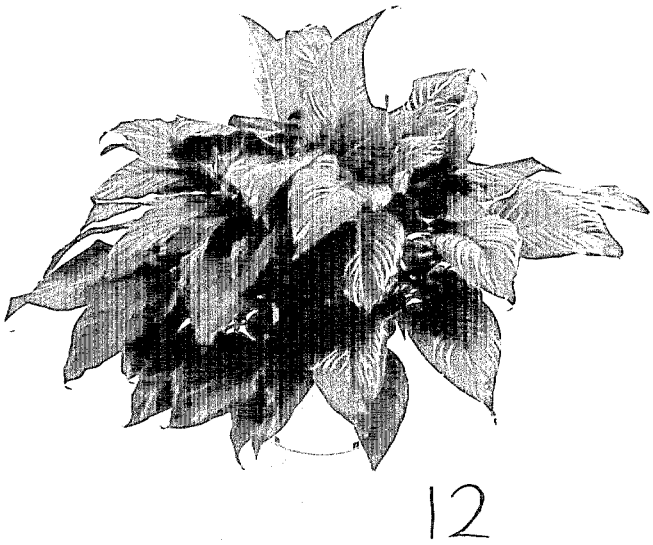
12
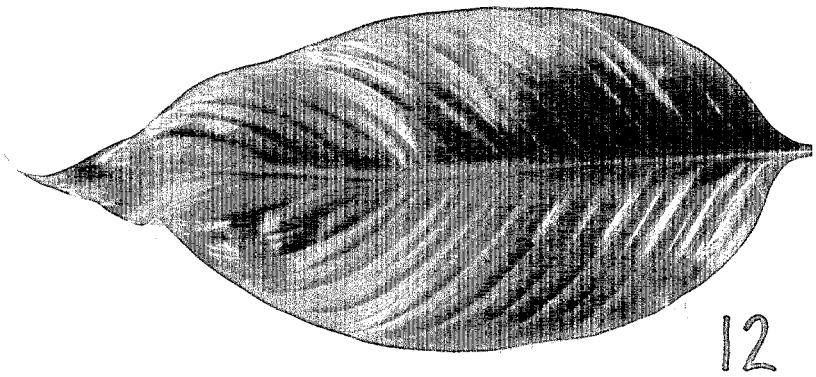
12

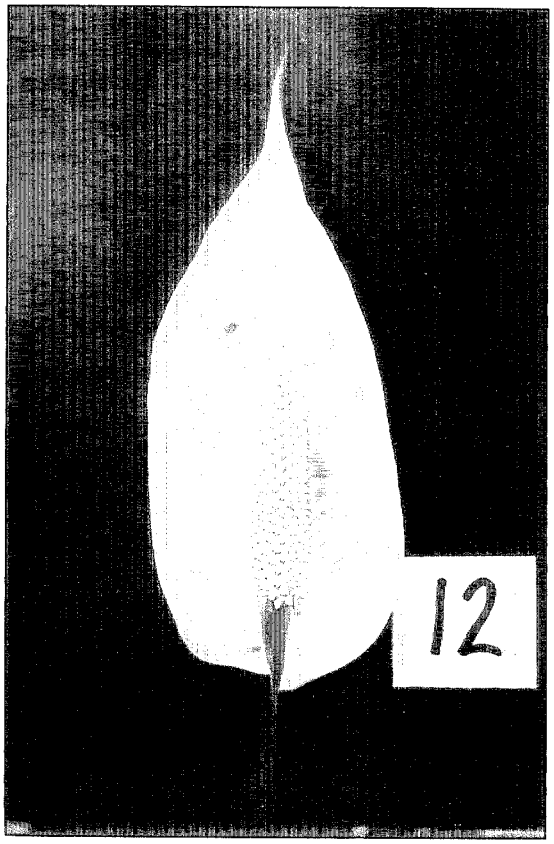
12